(12) United States Patent
Hardy et al.

(10) Patent No.: US 8,398,042 B2
(45) Date of Patent: Mar. 19, 2013

(54) CEILING-MOUNTED DOCKING DEVICE

(75) Inventors: Russell L. Hardy, Melville, NY (US); Allan Katz, Copiague, NY (US)

(73) Assignee: American Sterilizer Company, Mentor, OH (US)

( * ) Notice: Subject to any disclaimer, the term of this patent is extended or adjusted under 35 U.S.C. 154(b) by 384 days.

(21) Appl. No.: 12/730,540

(22) Filed: Mar. 24, 2010

(65) Prior Publication Data

US 2010/0243823 A1  Sep. 30, 2010

Related U.S. Application Data

(60) Provisional application No. 61/163,994, filed on Mar. 27, 2009.

(51) Int. Cl.
*A47H 1/10* (2006.01)

(52) U.S. Cl. ............................ 248/342; 248/906; 174/50

(58) Field of Classification Search ................... 248/342, 248/343, 344, 317, 906; 174/50, 559, 560, 174/561, 562, 563, 61, 62, 63, 64
See application file for complete search history.

(56) References Cited

U.S. PATENT DOCUMENTS

| | | | | |
|---|---|---|---|---|
| 3,566,872 A | | 3/1971 | Draeger et al. | 128/303.1 |
| 4,503,854 A | | 3/1985 | Jako | 128/303.1 |
| 5,025,126 A | | 6/1991 | Hansen | 219/125.1 |
| 5,470,139 A | * | 11/1995 | Hsiao | 312/140 |
| 6,096,025 A | | 8/2000 | Borders | 606/1 |
| 6,196,649 B1 | | 3/2001 | Block et al. | 312/209 |
| 6,431,515 B1 | * | 8/2002 | Gampe et al. | 248/324 |
| 6,639,789 B2 | * | 10/2003 | Beger | 606/46 |
| 6,817,585 B2 | * | 11/2004 | Wagner et al. | 248/324 |
| 6,899,442 B2 | | 5/2005 | Howell et al. | 362/147 |
| 7,097,145 B2 | * | 8/2006 | Turner | 248/281.11 |
| 7,122,032 B2 | | 10/2006 | Shinmura et al. | 606/34 |
| 7,191,992 B2 | | 3/2007 | Wagner et al. | 248/317 |
| 7,227,081 B2 | | 6/2007 | Bally et al. | 174/53 |
| 7,254,850 B2 | | 8/2007 | Newkirk et al. | 5/600 |
| 7,676,865 B2 | * | 3/2010 | Graham et al. | 5/503.1 |
| 7,726,823 B2 | * | 6/2010 | Rus et al. | 362/33 |
| 7,732,715 B2 | * | 6/2010 | Paolucci | 174/481 |
| 2007/0176060 A1 | | 8/2007 | White et al. | 248/124.1 |
| 2008/0030578 A1 | | 2/2008 | Razzaque et al. | 348/143 |

* cited by examiner

*Primary Examiner* — Terrell McKinnon
*Assistant Examiner* — Steven Marsh
(74) *Attorney, Agent, or Firm* — Kusner & Jaffe; Michael A. Centanni (57) ABSTRACT

The present invention provides a docking device for connecting to equipment. The docking device includes a first housing section having a plurality of leg sections extending from a surface thereof. A second housing section is attachable to the leg sections of the first housing section. The first housing section and the second housing section define an internal cavity of the docking device. The internal cavity is dimensioned to receive an electrical cable. The leg sections and the second housing section define an opening therebetween. The opening communicates with the internal cavity of the docking device. A panel is dimensioned to be received into the opening defined by the leg sections and the second housing section. The panel has a connector extending therethrough.

18 Claims, 10 Drawing Sheets

CEILING-MOUNTED DOCKING DEVICE

RELATED APPLICATIONS

This application claims the benefit of U.S. Provisional Application No. 61/163,994, filed Mar. 27, 2009, which is fully incorporated herein by reference.

FIELD OF THE INVENTION

The present invention relates to an apparatus for connecting to medical processing equipment, and, more particularly, to an overhead, ceiling-mounted docking device. The invention is particularly applicable for use in operating rooms during surgical procedures and will be described with reference thereto. However, it is to be understood that the present invention is useful in other applications where overhead access to electrical, audio/video or other connectors is needed.

BACKGROUND OF THE INVENTION

Improvements to imagining technology have allowed diagnostic devices, such endoscopes, to find increasing usage in surgical procedures. These diagnostic devices aid surgeons in viewing internal body parts of a patient during the surgical procedure. Conventional diagnostic devices, such as endoscopes, include electrical cables that allow the device to be connected to processing and display equipment. The processing equipment may convert the output of the diagnostic device for display on a monitor. The monitor is positioned near the surgeon so that the surgeon can view the monitor during the surgical procedure. In most applications, the processing equipment for the diagnostic device is placed on a movable cart. The monitor is typically mounted on the movable cart or is attached to the end of a ceiling-mounted surgical arm assembly.

Conventional processing equipment includes a power cord to connect the processing equipment to an electrical wall outlet in a surgical suite. In some circumstances, the processing equipment also includes audio/video cables to connect the processing equipment to wall-mounted audio/video ports. Cables in the wall of the surgical suite connect the audio/video ports to other devices in the surgical suite. For example, the cables may extend to monitors attached to ceiling-mounted surgical arms or to storage devices that store the output of the diagnostic devices.

During the course of a surgical procedure, it is not uncommon for the surgeon to reposition himself relative to a patient. However, as the surgeon moves, it is usually necessary to also reposition the cart that holds the processing equipment because of the limited length of the electrical cables from the diagnostic device to the processing equipment. As both the cart and the surgeon move, it is critical that the support personnel in the room also manage the movement of the cords and cables that extend from the processing equipment to the wall outlets. The support personnel may be required to pick up the cords and cables as the cart is moved around other equipment in the room. In some cases, it may be necessary to unplug the processing equipment from one wall outlet and re-plug the equipment into a more convenient wall outlet.

Movement of the processing equipment and cables creates a distraction for the surgeon and support staff. Moreover, cables on the floor create a trip hazard for the surgeon and support staff.

The present invention addresses these and other problems by providing a ceiling-mounted docking device to assist in the management of cords and cables in a surgical suite.

SUMMARY OF THE INVENTION

In accordance with a preferred embodiment of the present invention, there is provided a docking device for connecting to equipment. The docking device includes a first housing section having a plurality of leg sections extending from a surface thereof. A second housing section is attachable to the leg sections of the first housing section. The first housing section and the second housing section define an internal cavity of the docking device. The internal cavity is dimensioned to receive an electrical cable. The leg sections and the second housing section define an opening therebetween. The opening communicates with the internal cavity of the docking device. A panel is dimensioned to be received into the opening defined by the leg sections and the second housing section. The panel has a connector extending therethrough.

In accordance with another embodiment of the present invention, there is provided a ceiling-mounted assembly for connecting to equipment. The assembly includes a ceiling-mounted arm assembly that defines an internal passage extending therethrough. The arm assembly includes a central hub. A first arm member has a first end and a second end. The first end of the first arm member is attached to the hub. An articulating joint is rotatably attached to the second end of the first arm member. The articulating joint is rotatable relative to the first arm member. A second arm member has a first end and a second end. The first end of the second arm member is attached to the articulating joint. A docking device is attached to the second end of the second arm member. The docking device includes a first housing section having a plurality of leg sections extending from a surface thereof. The first housing section is attached to the second end of the second arm member. A second housing section is attachable to the leg sections of the first housing section. The first housing section and the second housing section define an internal cavity of the docking device. The internal cavity is dimensioned to receive an electrical cable. The leg sections and the second housing section define an opening therebetween. The opening communicates with the internal cavity of the docking device. A panel is dimensioned to be received into the opening defined by the leg sections and the second housing section. The panel has a connector extending therethrough.

One advantage of the present invention is a docking device for connecting a first device to a second, movable device, wherein the docking device may be placed in a plurality of positions.

Yet another advantage of the present invention is a docking device for connecting a first device to a second, movable device as described above, wherein the docking device is attached to an end of a ceiling-mounted arm assembly.

Another advantage of the present invention is a docking device for connecting a first device to a second, movable device as described above, wherein the docking device is easily configurable to include a variety of connectors for connecting to the second, movable device.

Another advantage of the present invention is a docking device for connecting a first device to a second, movable device, wherein the docking device is movable to maintain the connectors on the docking device in close proximity to the second, movable device.

Still another advantage of the present invention is a docking device for connecting a first device to a second, movable device, wherein the connectors on the docking device may be easily removed and replaced with other connectors.

Another advantage of the present invention is a docking device for connecting a first device to a second, movable device, wherein the connectors on the docking device are mounted to removable panels.

Yet another advantage of the present invention is a docking device for connecting a first device to a second, movable device, wherein the docking device may be positioned such that wires and/or cables from the second device are suspended above the floor.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
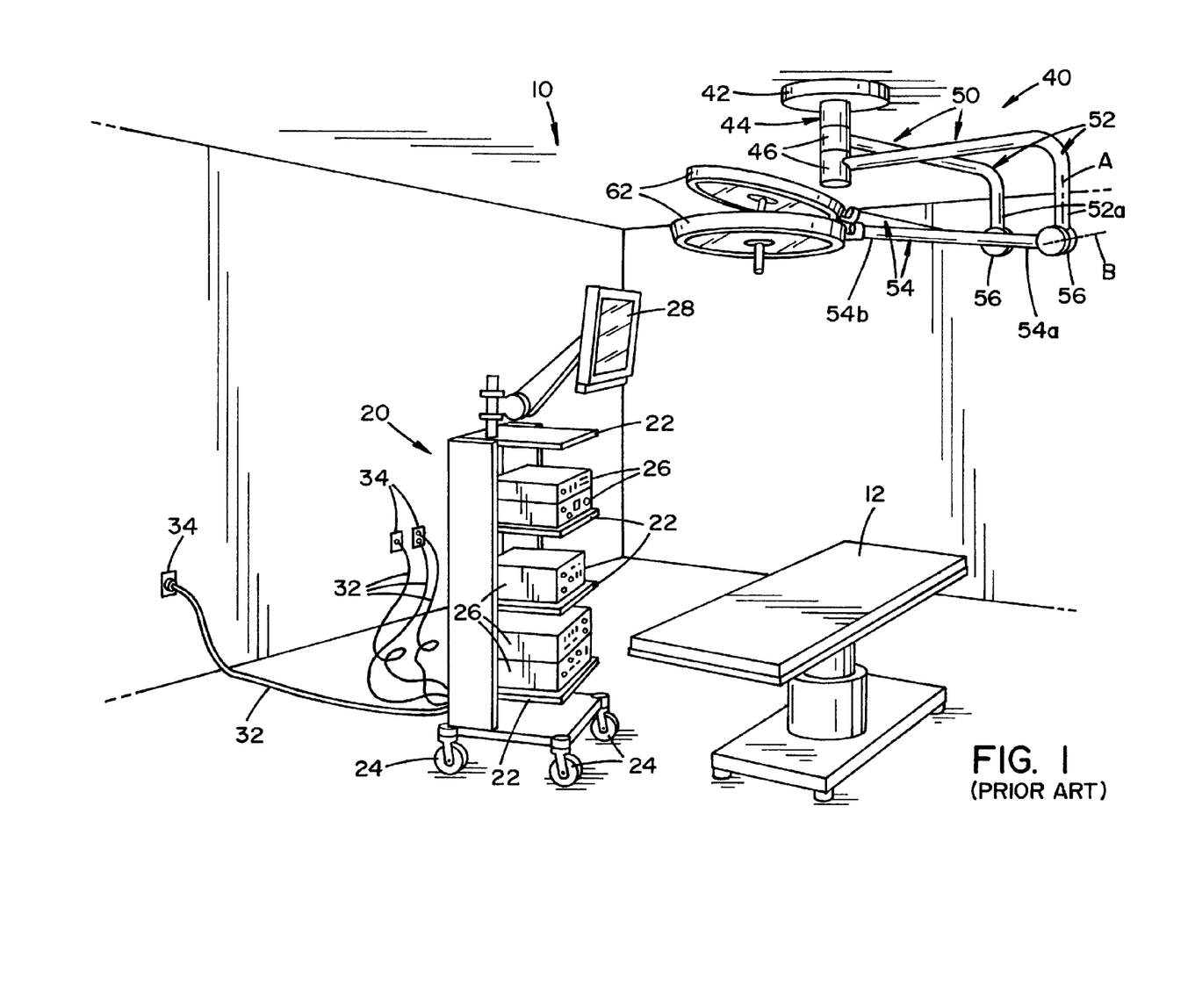
FIG. 1 is a perspective view of a conventional, surgical suite having a ceiling-mounted lighting system, a surgical table and a movable cart disposed therein.

Referring now to the drawings wherein the showings are for the purpose of illustrating a preferred embodiment of the invention only and not for the purpose of limiting the same. FIG. 1 shows a conventional, surgical suite 10 having a ceiling-mounted lighting system 40, a surgical table 12 and a movable cart 20.

Movable cart 20 includes a plurality of shelves 22 whereon processing equipment 26 is placed. Cart 20 also includes a plurality of wheels 24 that allow cart 20 to be moved within suite 10. A monitor 28 is attached to an upper portion of cart 20. A plurality of wires and/or cables 32 extend from processing equipment 26 to wall-mounted connectors 34.

Ceiling-mounted lighting system 40 includes a mounting plate 42 for securing system 40 to a ceiling of suite 10. A cylindrical column 44 extends downward from mounting plate 42. Cylindrical column 44 includes a plurality of hub sections 46. An arm assembly 50 extends from each hub section 46. Arm assembly 50 includes a first arm member 52, a second arm member 54 and an articulating joint 56 that connects first arm member 52 to second arm member 54.

First arm member 52 is an elongated tubular element that extends outwardly from hub section 46. In the embodiment shown, first arm member 52 is formed such that an end 52a of first arm member 52 is vertically orientated. First arm member 52 has an internal passageway (not shown) that extends therethrough. Second arm member 54 is connected to first arm member 52 by articulating joint 56. Second arm member 54 is an elongated tubular element that includes a first end 54a and a second end 54b. First end 54a is attached to articulating joint 56. In the embodiment shown in FIG. 1, a surgical lamp 62 is attached to second end 54b of second arm member 54. Second arm member 54 has an internal passageway (not shown) that extends therethrough.

Figure 3:
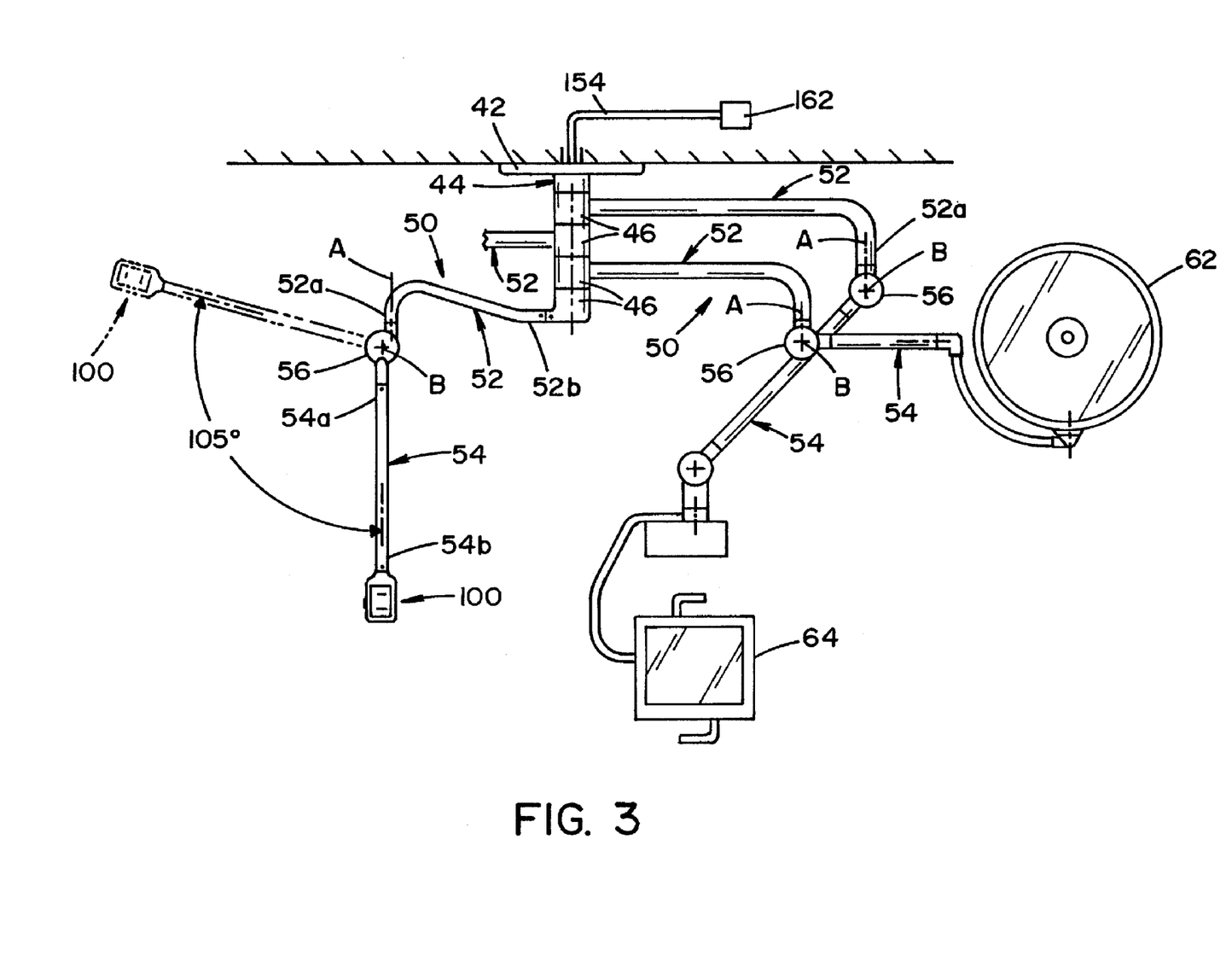
FIG. 3. is front plan view of a ceiling-mounted lighting system, showing a docking device according to the present invention in a first, vertical position and a second, rotated position.
Figure 4:
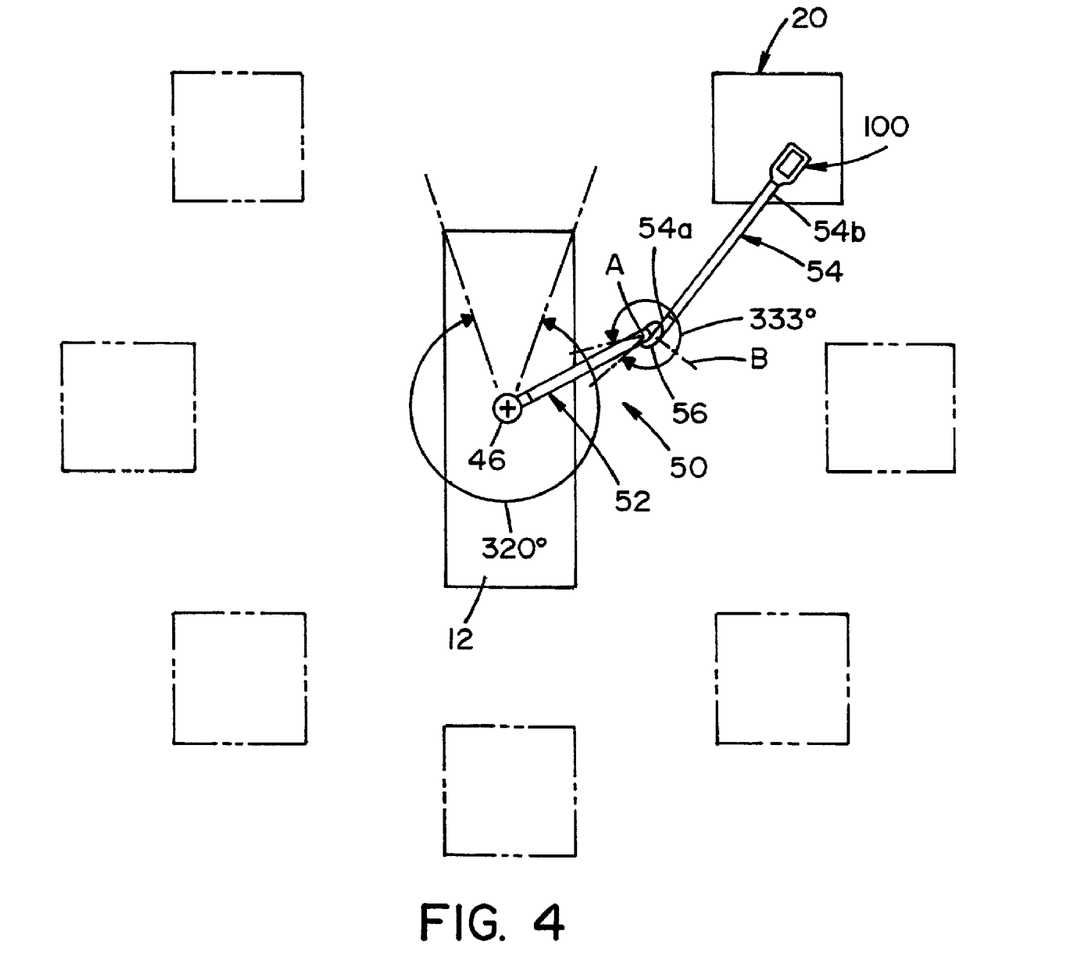
FIG. 4 is a top plan view of a ceiling-mounted lighting system, illustrating the range of movement of a docking device according to the present invention.
Figure 5:
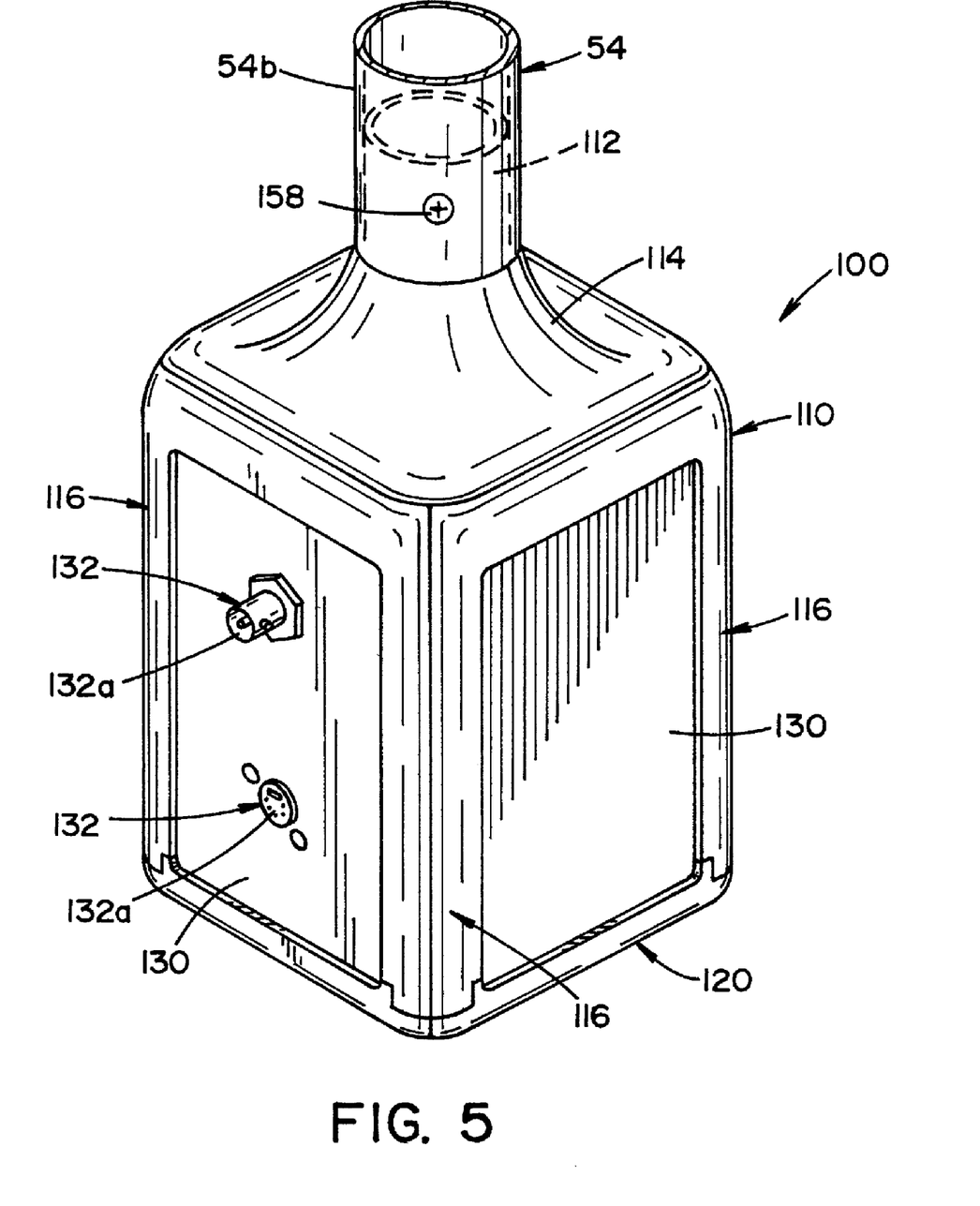
FIG. 5 is a top front perspective view of the docking device shown in FIG. 2.
Figure 6:
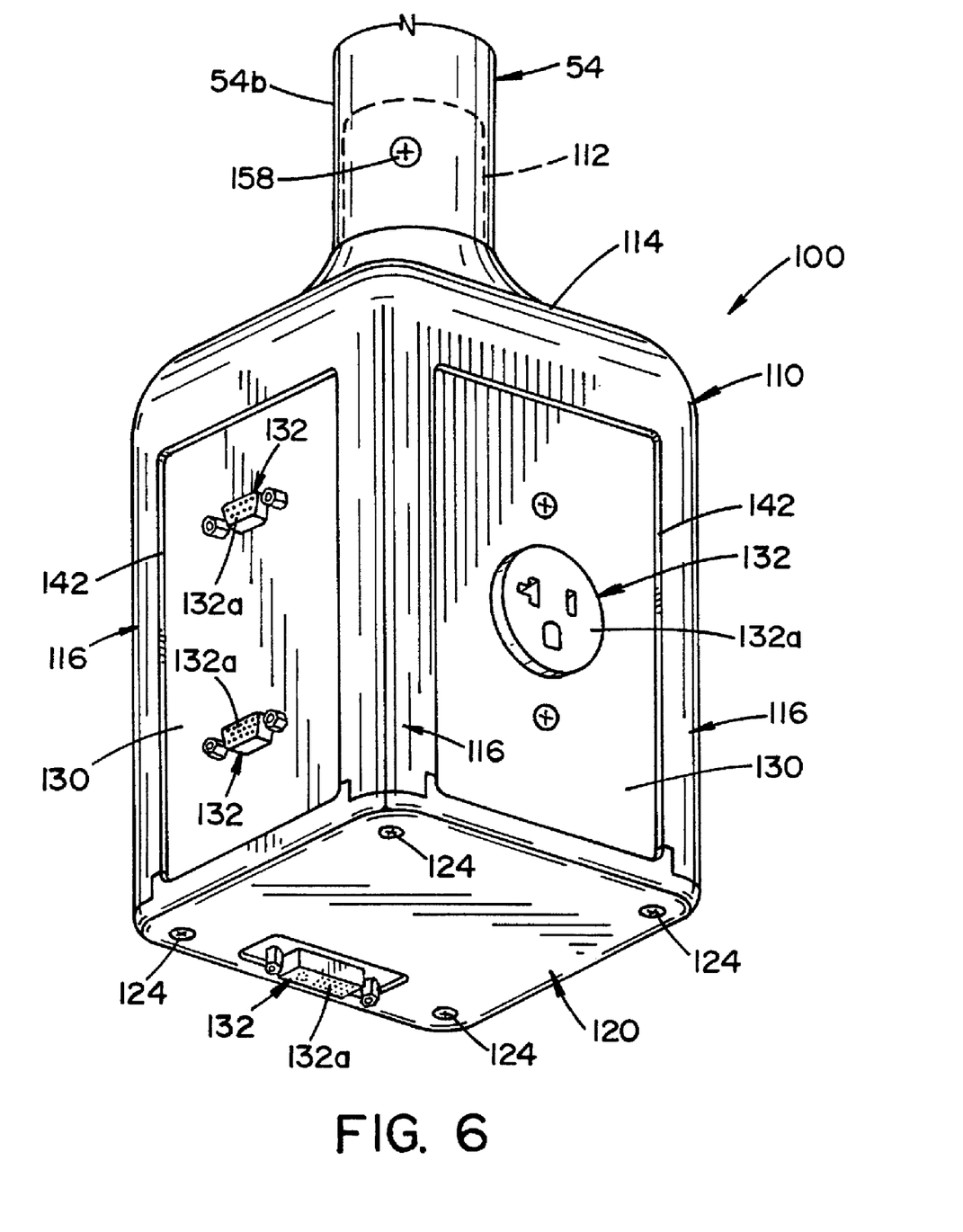
FIG. 6 is a bottom back perspective view of the docking device shown in FIG. 2.

Articulating joint 56 is provided to attach first arm member 52 to second arm member 54. Articulating joint 56 allows second arm member 54 to move relative to first arm member 52. In the embodiment shown, articulating joint 56 allows second arm member 54 to rotate about a vertical axis "A" defined by end 52a of first arm member 52 (as illustrated in FIG. 3). Articulating joint 56 also allows second arm member 54 to rotate about a central axis "B" of articulating joint 56 (as illustrated in FIGS. 3 and 4). Articulating joint 56 has an internal cavity (not shown) that communicates with the internal passageway in first arm member 52 and the internal passageway in second arm member 54.

Springs (not shown) are disposed in the inner passage of first arm member 52 and second arm member 54. The springs allow a distal end of arm assembly 50 to be positioned at a desired location.

Figure 2:
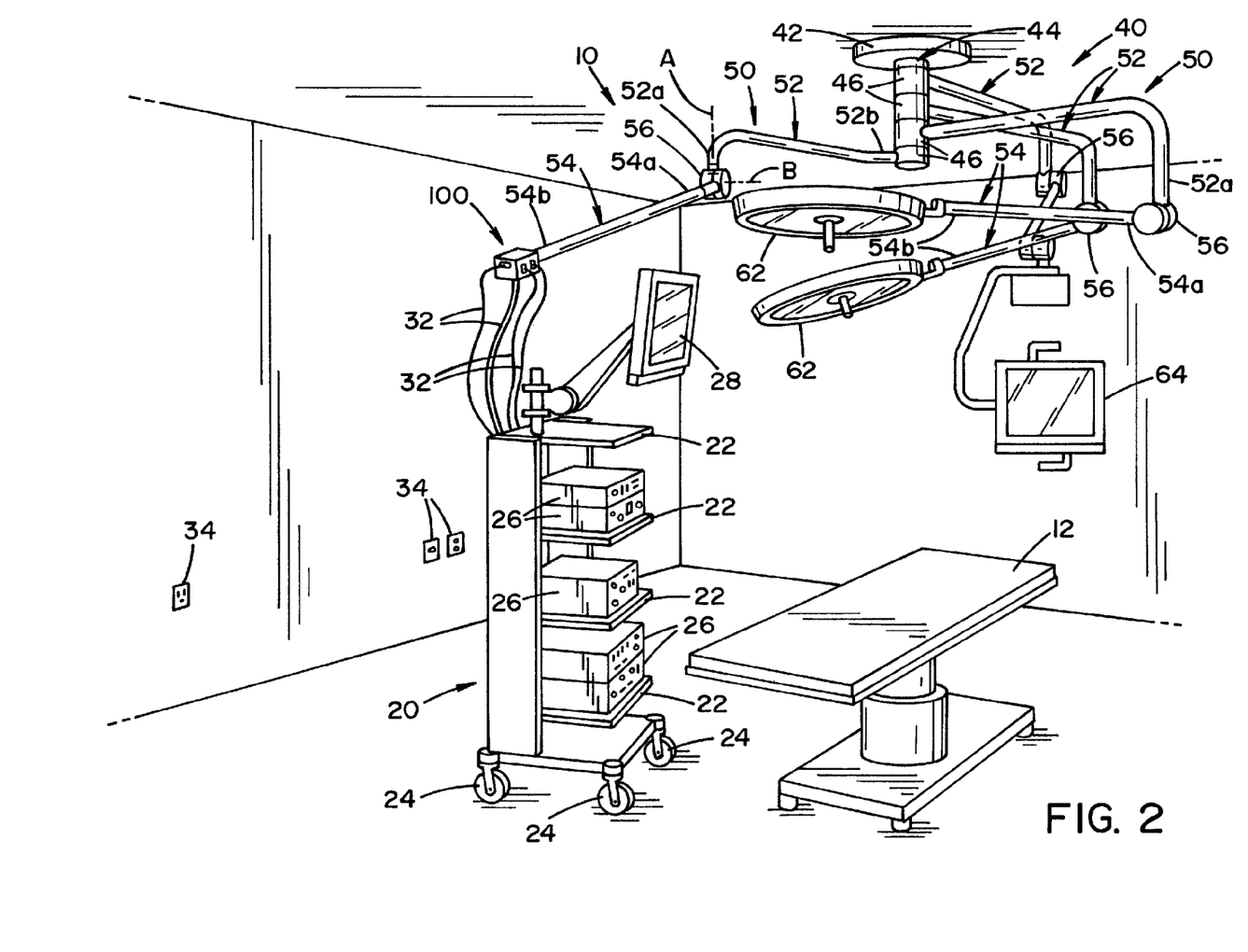
FIG. 2 is a perspective view of the conventional, surgical suite shown of FIG. 1, showing a docking device, according to the present invention, connected to processing equipment.

Referring now to FIG. 2, a docking device 100, according to the present invention, for attaching a first device to a second, movable device, is best seen. Docking device 100 is attached to a distal end of arm assembly 50. Docking device 100, as shown in FIGS. 5-11, is generally comprised of a first housing section 110, a second housing section 120 and a plurality of side panels 130 that are mountable to docking device 100.

Figure 9:
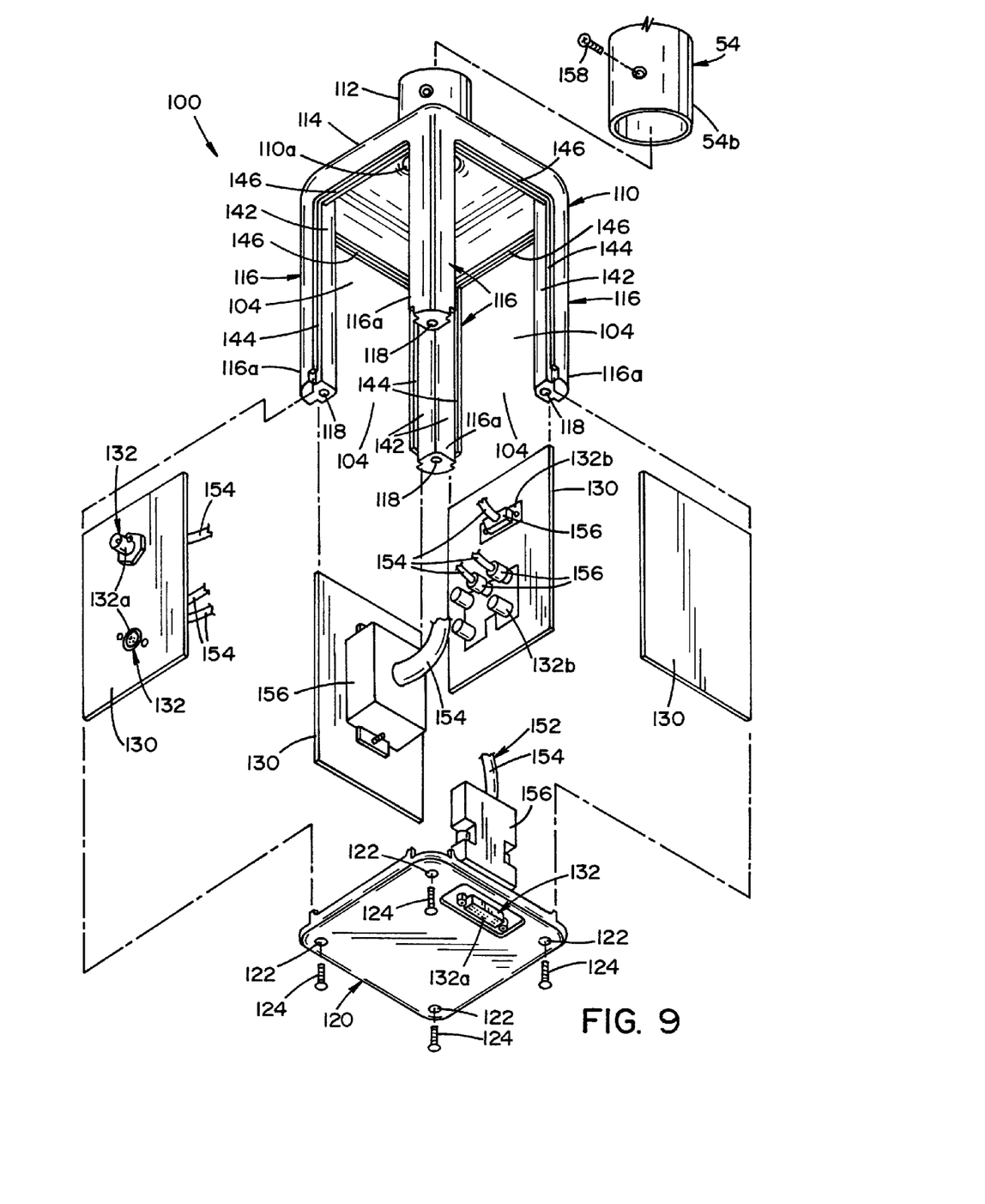
FIG. 9 is an exploded view of the docking device shown in FIG. 2.

As best seen in FIG. 9, first housing section 110 includes a tubular end section 112, an intermediate section 114 and a plurality of spaced-apart leg sections 116. In the embodiment shown, intermediate section 114 is funnel-shaped. An opening 110a, best seen in FIG. 10, extends through tubular end section 112 and through intermediate section 114. Spaced-apart leg sections 116 extend from intermediate section 114. Each leg-section 116 includes a threaded hole 118 that extends axially into a distal end 116a of leg section 116.

Second housing section 120, shown in FIG. 9, is attachable to leg sections 116 of first housing section 110. In the embodiment shown, second housing section 120 is a rectangular element with a hole 122 extending through each corner thereof. In this embodiment, a connector 132 extends through second housing section 120. Connector 132 is a conventional panel-mounted connector that includes a first connection port 132a on one side and a second connection port 132b on another side. It is contemplated that any number of connectors 132 may extend through second housing section 120.

Figure 10:
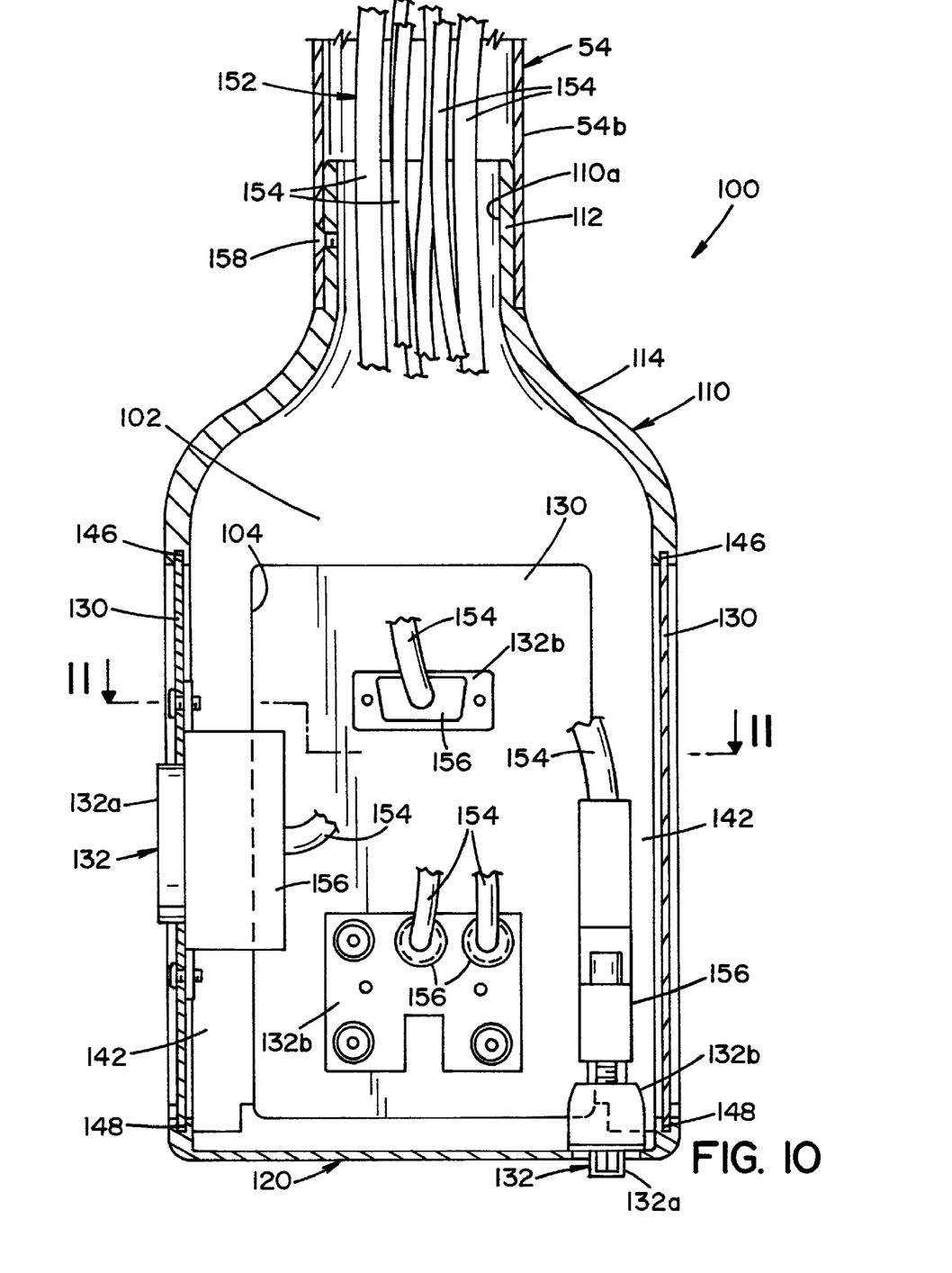
FIG. 10 is a side cross-sectional view of the docking device shown in FIG. 2.

Holes 118 in leg sections 116 and holes 122 in second housing section 120 are dimensioned and positioned to be in registry with each other when first housing section 110 and second housing section 120 are attached to each other. Fasteners 124 extend through holes 122 into threaded holes 118 to secure second housing section 120 to first housing section 110. As best seen in FIG. 10, first housing section 110 and second housing section 120 define an internal cavity 102 of docking device 100. As best seen in FIG. 9, a plurality of openings 104 is defined by intermediate section 114, spaced-apart leg sections 116 and second housing section 120. Openings 104 communicate with internal cavity 102 of docking device 100.

Side panel 130, shown in FIG. 9, is dimensioned to be received into opening 104 in docking device 100. In the embodiment shown, side panel 130 is a generally flat rectangular element. In another embodiment, connector 132 extends through side panel 130. It is contemplated that any number of connectors 132 may extend through side panel 130, as shown in FIGS. 5-8.

Figure 7:
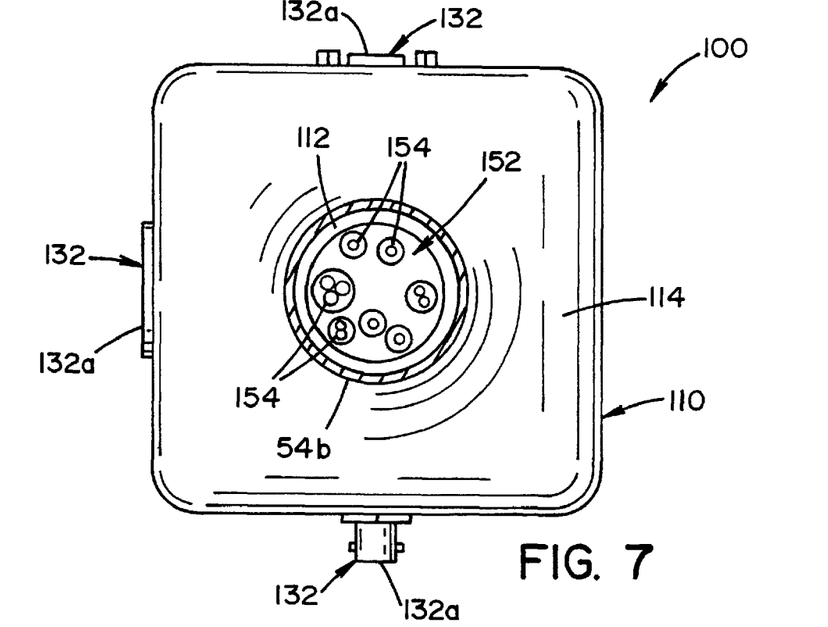
FIG. 7 is a top plan view of the docking device shown in FIG. 2.
Figure 8:
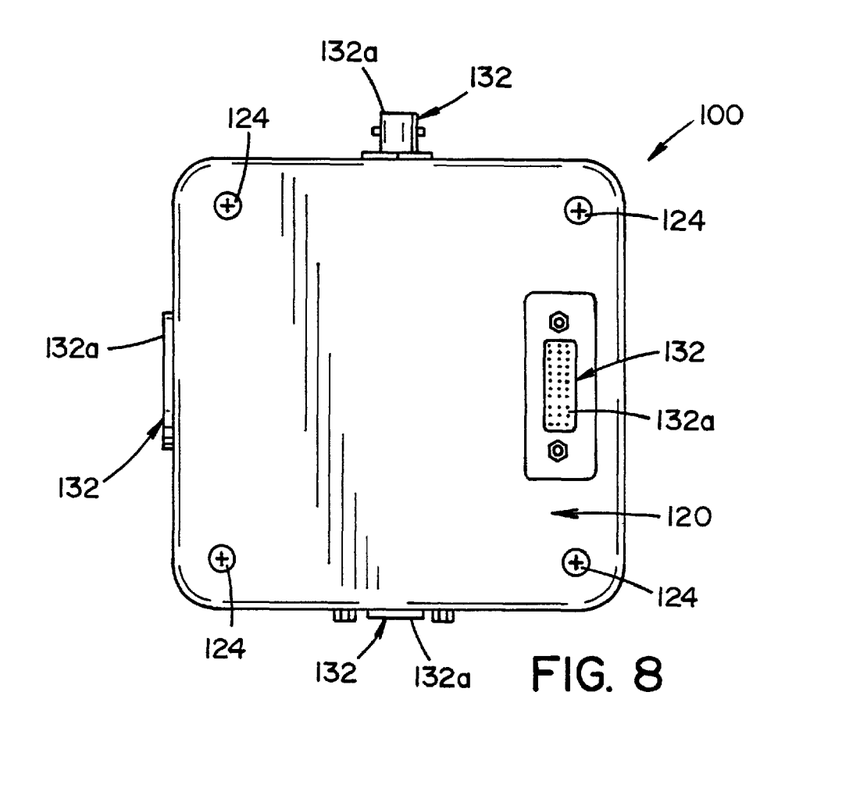
FIG. 8 is a bottom plan view of the docking device shown in FIG. 2.

A wire harness 152 is provided to extend through arm assembly 50 and into internal cavity 102 of docking device 100, as shown in FIG. 7. Wire harness 152 includes a plurality of wires and/or cables 154 with wire-mounted connectors 156 disposed at an end of each wire and/or cable 154. Connectors 156 are selected to connect to second connection port 132b of connector 132. Another end of each wire and/or cable 154 is attached to a piece of equipment 162. In the embodiment shown in FIG. 3, equipment 162 is a power supply. It is also contemplated that another end of wires and/or cables 154 is attached to a monitor, such as arm-mounted monitor 64, a storage device or other processing equipment.

Figure 11:
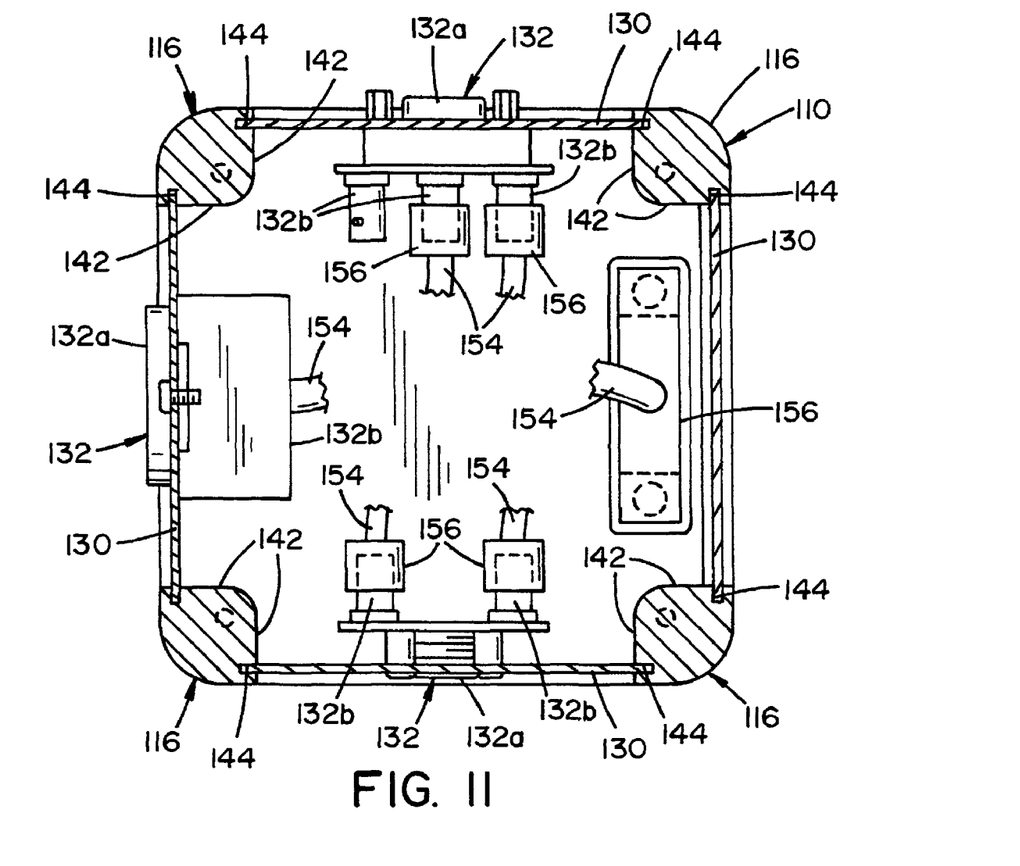
FIG. 11 is a sectional view taken along lines 11-11 of FIG. 10.

Docking device 100 is assembled by first connecting second connection port 132b of connector 132 to wire-mounted connector 156 on wire harness 152. Side panel 130 is then attached to docking device 100 by placing side panel 130 into opening 104 of docking device 100. In the embodiment shown, four (4) leg sections 116 extend from intermediate section 114. Adjacent pairs of leg sections 116 each include opposing planar faces 142 with opposing slots 144 formed therein, as best seen in FIG. 11. As best seen in FIG. 10, a slot 146 is also formed in a portion of first housing section 110 between adjacent leg sections 116. Another slot 148 is formed in a portion of second housing section 120. Slots 144, 146, 148 are dimensioned and positioned to receive a side panel 130 therein, as shown in FIGS. 10 and 11. To secure side panel 130 into opening 104 of docking device 100, side panel 130 is first slid into slots 144, 146 in first housing section 110. Then, second housing section 120 is attached to first housing section 110 such that side panel 130 is received into slot 148 in second housing section 120. It is also contemplated that other devices, such as fasteners, may extend through side panel 130 and docking device 100 to secure side panel 130 into opening 104.

As shown in FIG. 9, end section 112 of first housing section 110 is dimensioned to attach to second end 54b of second arm member 54. A fastener 158 extends through a hole in end section 112 to secure docking device 100 to second arm member 54.

As described above, second arm member 54 of arm assembly 50 is movable relative to ceiling-mounted lighting system 40. Since docking device 100 is mounted to second arm member 54, docking device 100 also is movable relative to ceiling-mounted lighting system 40. In other words, docking device 100 is rotatable about 320 degrees around a central axis of the lighting system 40 (as illustrated in FIG. 4). Docking device 100 is also rotatable about 333 degrees about central axis "A" of first arm member 52 (as illustrated in FIG. 4). Moreover, docking device 100 is rotatable about 105 degrees, with respect to central axis "B" of articulating joint 56 (as illustrated in FIG. 3). In this respect, docking device 100 may be positioned in a plurality of positions in surgical suite 10.

The present invention shall now be described with respect to the operation of the docking device 100. At the beginning of the procedure, the support staff positions docking device 100 at a location in close proximity to a movable cart 20 that contains processing equipment 26. Wires and/or cables 32 from processing equipment are then connected to first connection port 132a of a desired connector 132 on docking device 100. Wire harness 152, in turn, connects processing equipment 26 to a desired piece of equipment, e.g., a monitor, a storage device or a source of power.

As described above, during the course of an operation a surgeon may desire to move about surgical site 10. According to the present invention, the support staff can simultaneously reposition movable cart 20 and docking device 100 to a convenient location. The present invention does not require support staff to remove cables from the floor or to disconnect or re-connect equipment as the cart is moved in the surgical suite. Moreover, by connecting the cables and chords to the docking device, the surgeon and staff do not have to worry about tripping over chords.

The present invention therefore provides a docking device for connecting a first device to a second, movable device wherein the docking device is movable to maintain connectors on the docking device in close proximity to the second, movable device. Another advantage of the present invention is a docking device for connecting a first device to a second, movable device, wherein the connectors are mounted on removable panels, thereby allowing the connectors to be easily upgraded or retrofitted.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A docking device for connecting to equipment, said docking device comprised of:
   a first housing section having a plurality of leg sections extending from a surface thereof;
   a second housing section attachable to said leg sections of said first housing section, wherein said first housing section and said second housing section define an internal cavity of a docking device, said internal cavity dimensioned to receive an electrical cable, and wherein said leg sections and said second housing section define an opening therebetween, said opening communicating with said internal cavity of said docking device; and
   a panel dimensioned to be received into said opening defined by said leg sections and said second housing section, said panel having a connector extending therethrough, wherein said connector in said panel includes a first connection port disposed to one side of said panel for connecting to said equipment and a second connector port disposed to an opposite side of said panel for connecting to said electrical cable.

2. A docking device as defined in claim 1, wherein said docking device is attached to a distal end of a ceiling-mounted arm assembly.

3. A docking device as defined in claim 1, wherein a pair of said leg sections includes opposing planar surfaces with a groove formed in each of said planar surfaces, each of said grooves dimensioned to receive an edge of said panel.

4. A docking device as define in claim 1, wherein said second housing section includes a groove dimensioned to receive an edge of said panel.

5. A docking device as defined in claim 1, wherein a portion of said first housing section between a pair of said plurality of legs includes a groove dimensioned to receive an edge of said panel.

6. A docking device as defined in claim 1, wherein said connector is a power connector.

7. A docking device as defined in claim 1, wherein said connector is an audio connector.

8. A docking device as defined in claim 1, wherein said connector is a video connector.

9. A ceiling-mounted assembly for connecting to equipment, said assembly comprised of:
 a ceiling-mounted arm assembly defining an internal passage extending therethrough, said arm assembly comprised of:
  a central hub,
  a first arm member having a first end and a second end, said first end of said first arm member attached to said hub,
  an articulating joint rotatably attached to said second end of said first arm member, said articulating joint rotatable relative to said first arm member, and
  a second arm member having a first end and a second end, said first end of said second arm member attached to said articulating joint; and
 a docking device attached to said second end of said second arm member, said docking device comprised of:
  a first housing section having a plurality of legs sections extending from a surface thereof, said first housing section attached to said second end of said second arm member,
  a second housing section attachable to said leg sections of said first housing section, wherein said first housing section and said second housing section define an internal cavity of said docking device, said internal cavity of said docking device dimensioned to receive an electrical cable, and wherein said leg sections and said second housing section define an opening therebetween, said opening communicating with said internal cavity of said docking device, and
  a panel dimensioned to be received into said opening defined by said leg sections and said second housing section, said panel having a connector extending therethrough, wherein said connector in said panel includes a first connection port disposed to one side of said panel for connecting to said equipment and a second connector port disposed to an opposite side of said panel for connecting to said electrical cable.

10. An assembly as defined in claim 9, wherein said assembly is attached to a bottom of a ceiling-mounted lighting system.

11. An assembly as defined in claim 10, wherein said assembly is rotatable about 320 degrees relative to a vertical axis of said ceiling-mounted lighting system.

12. An assembly as defined in claim 9, wherein a plurality of wires extend into said internal cavity of said docking device.

13. An assembly as defined in claim 12, wherein at least one of said plurality of wires includes a connector for attaching to said connector in said panel.

14. An assembly as defined in claim 12, wherein said plurality of wires extend from said docking device to a monitor.

15. An assembly as defined in claim 9, wherein a pair of said leg sections includes opposing planar surfaces with a groove formed in each of said planar surfaces, each of said grooves dimensioned to receive an edge of said panel.

16. An assembly as defined in claim 9, wherein said connector is a power connector.

17. An assembly as defined in claim 9, wherein said connector is an audio connector.

18. An assembly as defined in claim 9, wherein said connector is a video connector.

\* \* \* \* \*